US00PP35403P2

(12) United States Plant Patent
van Noort

(10) Patent No.: US PP35,403 P2
(45) Date of Patent: Sep. 26, 2023

(54) COREOPSIS PLANT NAMED 'MVNC1904'

(50) Latin Name: *Coreopsis grandiflora*
Varietal Denomination: MVNC1904

(71) Applicant: Marco van Noort, Warmond (NL)

(72) Inventor: Marco van Noort, Warmond (NL)

(73) Assignee: MARCO VAN NOORT BREEDING BV, Warmond (NL)

( * ) Notice: Subject to any disclaimer, the term of this patent is extended or adjusted under 35 U.S.C. 154(b) by 0 days.

(21) Appl. No.: 17/948,459

(22) Filed: Sep. 20, 2022

(30) Foreign Application Priority Data

Feb. 7, 2022 (QZ) ..... PBR 20220390

(51) Int. Cl.
*A01H 5/02* (2018.01)
*A01H 6/14* (2018.01)

(52) U.S. Cl.
USPC ..... Plt./417
CPC ..... *A01H 6/14* (2018.05)

(58) Field of Classification Search
USPC ..... Plt./417
CPC ..... A01H 6/14; A01H 5/02
See application file for complete search history.

*Primary Examiner* — Keith O. Robinson
(74) *Attorney, Agent, or Firm* — Penny J. Aguirre

(57) ABSTRACT

A new cultivar of hybrid *Coreopsis* plant named 'MVNC1904' that is characterized by its compact, plant habit, its long flowering period from late spring to early autumn in The Netherlands (commences early in the season), its inflorescences with ray florets that are cherry red in color with yellow margins, its resistance to powdery mildew, its high tolerance to heat and humidity, and its healthy foliage that maintains its bright green appearance.

2 Drawing Sheets

Botanical classification: *Coreopsis grandiflora*.
Variety denomination: 'MVNC1904'.

CROSS-REFERENCE TO RELATED APPLICATIONS

This application claims priority to European Community Plant Variety Office (CPVO) Plant Breeder's Rights Application No. 2022/0390 filed on Feb. 7, 2022, under 35 U.S.C. 119(f), the entire contents of which is incorporated by reference herein. This application is also co-pending with U.S. Plant Patent Applications filed for plants derived from the same breeding program that are entitled *Coreopsis* Plant Named 'MVNC1902' (U.S. Plant Pat. No. 35,041), *Coreopsis* Plant Named 'MVNC1823' (U.S. Plant Pat. No. 35,088), and *Coreopsis* Plant Named 'MVNC1906' (U.S. Plant Pat. No. 35,140).

BACKGROUND OF THE INVENTION

The present invention relates to a new and distinct cultivar of *Coreopsis* plant, botanically of hybrid origin and known as *Coreopsis grandiflora* 'MVNC1904' and will be referred to hereinafter by its cultivar name, 'MVNC1904'. The new cultivar of *Coreopsis* is an herbaceous perennial grown for landscape and container use.

The new cultivar arose from an ongoing breeding program conducted by the Inventor in Warmond, The Netherlands. The goal of the breeding program is to develop new cultivars of *Coreopsis grandiflora* that are early flowering and have dependable perennial habits, an abundance of flowers, healthy foliage with powdery mildew resistance combined with unique inflorescence coloration. 'MVNC1904' was selected by the Inventor as a seedling in a trial garden in Warmond, The Netherlands in July of 2017. The new cultivar arose from open pollination of unnamed (not patented) seedlings of *Coreopsis grandiflora* in the inventors breeding program. The seeds were pooled after collection and therefore the exact parents are unknown.

Asexual propagation of the new cultivar was first accomplished by stem cuttings in Lisse, The Netherlands in 2021 under the direction of the Inventor. Asexual propagation by stem cuttings has determined that the characteristics of the new cultivar are stable and are reproduced true to type in successive generations.

SUMMARY OF THE INVENTION

The following traits have been repeatedly observed and are determined to be the characteristics of the new cultivar. These attributes in combination distinguish 'MVNC1904' as a unique cultivar of *Coreopsis*.

1. 'MVNC1904' exhibits a compact plant habit.
2. 'MVNC1904' exhibits a long flowering period from late spring to early autumn in The Netherlands (commences early in the season).
3. 'MVNC1904' exhibits inflorescences with ray florets that are cherry red in color with yellow margins.
4. 'MVNC1904' exhibits an abundance of inflorescences that are large in size.
5. 'MVNC1904' exhibits resistance to powdery mildew.
6. 'MVNC1904' exhibits a high tolerance to heat and humidity.
7. 'MVNC1904' exhibits healthy foliage that maintains its bright green appearance.

'MVNC1904' can be most closely compared to *Coreopsis grandiflora* cultivar 'Sonnenkind' (not patented) and cultivars derived from the same crosses; 'MVNC1902', 'MVNC1823', and 'MVNC1906'. 'Sonnenkind' differs from 'MVNC1904' in having a lower resistance to powdery mildew, foliage that is not as healthy, and in producing fewer inflorescences. 'MVNC1902' differs from 'MVNC1904' in having inflorescences with ray florets that are bright red in color with yellow-orange margins. 'MVNC1823' differs from 'MVNC1904' in having inflorescences with ray florets that are yellow in color with red centers. 'MVNC1906' differs from 'MVNC1904' in having inflorescences with ray florets that are light yellow in color with dark red centers.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales that fall within a one-year grace period prior to the filing date. Publications include listings on websites by Plantipp and Quality Cuttings.

BRIEF DESCRIPTION OF THE DRAWINGS

The accompanying color photographs illustrate the overall appearance and distinct characteristics of the new *Coreopsis*. The photographs were taken of a 1-year-old plant of 'MVNC1904' as grown outdoors in a 17 cm container in Warmond, The Netherlands.

The photograph in FIG. 1 provides a view of the plant habit of 'MVNC1904' in bloom.

Figure 1:
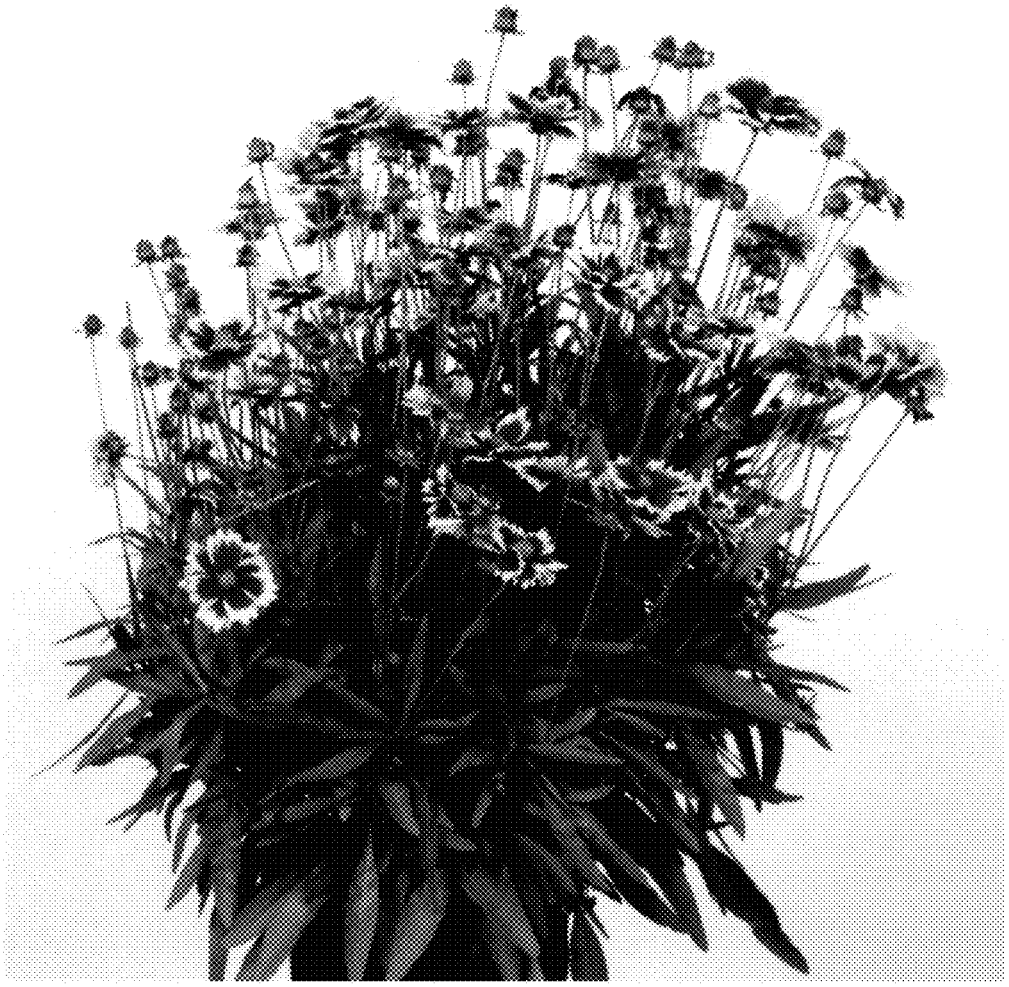
Figure 2:
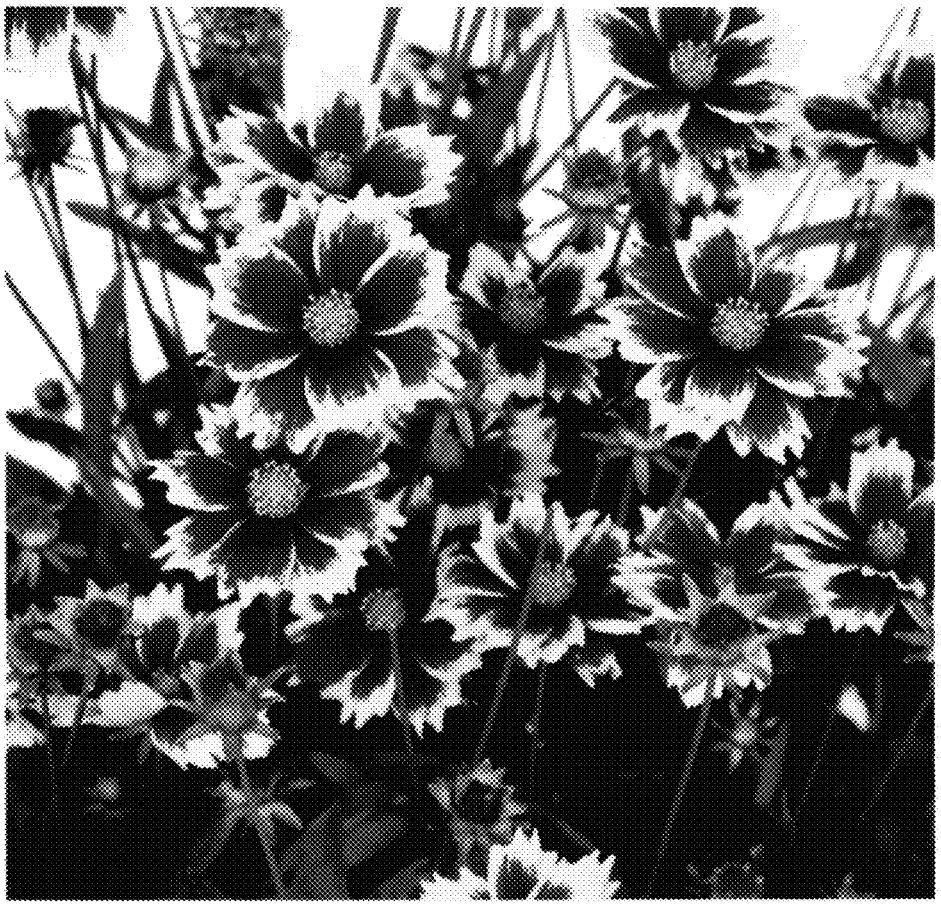

The photograph in FIG. 2 provides a close-up view of the inflorescences of 'MVNC1904'.

The colors in the photographs are as close as possible with the photographic and printing technology utilized and the color values cited in the detailed botanical description accurately describe the colors of the new *Coreopsis*.

DETAILED BOTANICAL DESCRIPTION

The following is a detailed description of 1-year-old plants of 'MVNC1904' as grown outdoors in 17 cm containers in Warmond, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Blooms from early late spring to early autumn in the Netherlands.

*Plant type*.—Herbaceous perennial.

*Plant habit*.—Clump-forming, bushy and compact, upright leafy flowering stems with inflorescences held above the foliage.

*Height and spread*.—Reaches an average of 50 cm in height and 43.8 cm in width.

*Cold hardiness*.—At least to U.S.D.A Zone 4.

*Diseases and pests*.—Resistance to powdery mildew (*Podosphaera macularis*), no susceptibility or resistance to pests has been observed.

*Root description*.—Fibrous and fine, NN155A in color.

*Propagation*.—Stem cuttings.

*Root development*.—An average of 10 days for root initiation, an average of 20 weeks to produce a marketable plant.

*Growth rate*.—Moderate to highly vigorous.

Branch description:

*Branch shape*.—Rounded, moderately axially ribbed.

*Branch color*.—144A.

*Branch size*.—Main and secondary stems; an average of 13.9 cm in length and 3.5 mm in width.

*Branch strength*.—Very strong.

*Branch surface*.—Glabrous.

*Branch aspect*.—Average of 30° to vertical.

*Branching quantity*.—An average of 23 main branches, 5 secondary branches per main stem.

*Internode length*.—An average of 6.1 cm.

Foliage description:

*Leaf division*.—Simple, 25% of leaves trifoliate.

*Leaf and leaflet margins*.—Entire.

*Leaf size*.—8.3 cm in length, 2 cm in width, lateral leaflets of trifoliate leaves; 2.9 cm in length, 8 mm in width.

*Leaf shape*.—Lanceolate, 25% of leaves trifoliate with lanceolate leaflets.

*Leaf and leaflet base*.—Long attenuate.

*Leaf and leaflet apex*.—Bluntly acute to acute.

*Leaf and leaflet venation*.—Pinnate, color upper surface; 146B, lower surface 146A to 146B.

*Leaf attachment*.—Petiolate.

*Leaf arrangement*.—Opposite.

*Leaf and leaflet surface*.—Upper surface very slightly glossy, smooth, slightly leathery, lower surface slightly glossy to moderately glossy, smooth, slightly leathery, sparsely pubescent with short thin hairs, 0.5 mm in length, too small to measure color.

*Leaf and leaflet color*.—Young upper surface 138A, young lower surface 146B, mature upper surface 137A to 137B, mature lower surface 147B.

*Petioles*.—Average of 3.7 cm in length, 2.5 mm in width, v-shaped, both surfaces smooth and glabrous, upper surface 146B in color, lower surface 144A in color, margins sparsely pubescent with short thin hairs an average of 1 mm in length and too small to measure color.

Flower description:

*Inflorescence type*.—Terminal capitulum consisting of ray florets and disc florets.

*Lastingness of inflorescence*.—Average of 10 days.

*Fragrance*.—Faint, pleasant.

*Quantity of inflorescences*.—1 per lateral stem, 140 per plant.

*Inflorescence size*.—1.7 cm in height, 6 cm in diameter, disc diameter 1.2 cm.

*Inflorescence buds*.—Broad obovate in shape, an average of 9 mm in depth and 8 mm in diameter, dull surface; color; 152A, blotched 152C to 152D.

*Peduncle*.—Rounded in shape, moderately strong, held in a vertical angle, an average of 15.3 cm in length and 2 mm in diameter, 143C and 144A in color, smooth, slightly glossy and glabrous surface.

Phyllaries (involucral bracts):

*Phyllary number*.—2 rows; total of 16, upper row 8, lower row 8.

*Phyllary size*.—Upper phyllaries; an average of 1 cm in length and 4.5 mm in width, lower phyllaries; an average of 8 mm in length and 2.5 mm in width.

*Phyllary color*.—Upper phyllaries upper surface; 152B, upper phyllaries lower surface; 146B, upper ⅔rd 152C, margins 154B, lower phyllaries upper surface; 144A, lower phyllaries lower surface; 143A to 144A.

*Phyllary texture*.—Both surfaces smooth, glabrous, moderately glossy.

*Phyllary apex*.—Acute.

*Phyllary base*.—Cuneate.

*Phyllary shape*.—Upper phyllaries; ovate, lower phyllaries; narrow ovate.

Ray florets:

*Number*.—10, (varying between 8 and 13).

*Shape*.—Obovate, rotate.

*Size*.—An average of 2.6 cm in length and 1.7 cm in width.

*Apex*.—Cleft into 3 lobes, tips of central lobe emarginate, tips of lateral lobes bluntly acute.

*Base*.—Rounded.

*Margins*.—Entire.

*Aspect*.—Rotate.

*Texture*.—Upper surface; matte, glabrous, velvety, slightly to moderately carinate, lower surface; very slightly glossy, glabrous, non-velvety.

*Color*.—When opening upper surface; 3A, lower ⅔rd 187A to 187C, when opening lower surface; 187C to 197D, top 3A, base 12A, base tinged 183C, when fully open upper surface; 5B, lower half between 59A and 187A, fully open lower surface; 197D, upper ⅓rd 4A, base 183C, fading to 197C to 197D, upper ⅓rd 4A, base 183B.

Disc florets (male and female):

*Number*.—An average of 90.

*Shape*.—Tubular.

*Base*.—Lower 85% fused.

*Size*.—About 6 mm in length and 2.5 mm in width.

*Apex*.—Acute.

*Surface*.—Glabrous, moderately glossy.

*Margins*.—Entire.

*Color*.—When opening upper and lower surface; 15A, lower half 153D, fully open upper and lower surface; 15A, mid-section 15D, base 153D.

*Receptacle*.—Flattened, average of 2 mm in height, 4 mm in diameter, 147D in color.

*Receptacle spines*.—Linear, 90 per disc floret, soft, narrow acute apex, narrow cuneate base, surface glabrous, moderately glossy, color; apex 13A to 13B, mid-section 145C, base 157D.

Reproductive organs:

*Gynoecium*.—1 Pistil; an average of 7.5 mm in length, style; 7 mm in length, 154C in color, stigma; unequal decurrent, 15A in color, ovary; 156C, base and top tinged 181D.

*Androecium*.—5 stamens, filament; 3 mm in length, 166A in color, anther; linear, 4 mm in length, 14D in color, pollen; moderate in quantity and 15A in color.

*Seed*.—Seed development has not been observed.

It is claimed:

1. A new and distinct cultivar of *Coreopsis* plant named 'MVNC1904' as herein illustrated and described.

* * * * *